United States Patent
Nobori et al.

(10) Patent No.: US 6,303,815 B1
(45) Date of Patent: Oct. 16, 2001

(54) PROCESS FOR PREPARING PHOSPHINE OXIDES AND PROCESS FOR PURIFYING THE SAME

(75) Inventors: Tadahito Nobori; Isao Hara, both of Kanagawa; Katsuhiko Funaki, Chiba; Takaomi Hayashi, Chiba; Atsushi Shibahara, Chiba; Shinji Kiyono, Chiba; Kazumi Mizutani, Kanagawa; Usaji Takaki, Kanagawa, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/548,624

(22) Filed: Apr. 13, 2000

(30) Foreign Application Priority Data

Apr. 13, 1999 (JP) .................................................. 11-105431

(51) Int. Cl.$^7$ ...................................................... C07F 9/22
(52) U.S. Cl. ................................................................ 564/14
(58) Field of Search .................................................. 564/14

(56) References Cited

FOREIGN PATENT DOCUMENTS

| 0972776 | 1/2000 | (EP) . |
| 772178 | 4/1957 | (GB) . |

OTHER PUBLICATIONS

CA:104:207357 abs of Zh. Obsch. Khim. by Koidan et al 55(7) pp. 1633–4, 1985.*

Koidan, G.N. "Methylation of the phosphoryl group by methyl iodine"Journal of General Chemistry USSR., vol. 55, No. 7, p. 1453, XP002143529, Jan. 10, 1986.

* cited by examiner

*Primary Examiner*—Jean F. Vollano
(74) *Attorney, Agent, or Firm*—Burns, Doane, Swecker, & Mathis, L.L.P.

(57) ABSTRACT

A process for preparing phosphine oxides by reacting iminophosphoranes with phosphorus oxytrichloride by which highly purified phosphine oxides can be obtained industrially in a higher yield. Specifically, phosphine oxides are prepared in such a manner that iminophosphoranes are reacted with phosphorus oxytrichloride using an aprotic organic solvent with permittivity 2.2 or more at 20° C. as a solvent under special reaction conditions to give a liquid reaction product containing phosphine oxides and aminophosphonium chlorides which are yielded as a by-product at the same time as the phosphine oxides, and the above described chlorides are removed from the above described liquid reaction product by a solid-liquid separation process, and the solution having been subjected to the solid-liquid separation process is washed with water.

12 Claims, No Drawings

PROCESS FOR PREPARING PHOSPHINE OXIDES AND PROCESS FOR PURIFYING THE SAME

BACKGROUND OF THE INVENTION

1. Technical Field

This invention relates to a process for preparing phosphine oxides having the general formula (2) which comprises reacting iminophosphoranes having the general formula (1) with phosphorus oxytrichloride and to a process of purifying the above described phosphine oxides. The present inventors previously found that the above described phosphine oxides are very effective as polymerization catalysts for polymerizing alkylene oxide compounds, as catalysts for producing oxyalkylene derivatives from epoxy compounds, or as curing catalysts for curing the raw material resin for IC sealing, and already filed an application for a patent on each of the above described catalysts (Japanese Patent Application No. 10-106745, Japanese Patent Laid-Open Nos. 11-302371 or 11-322901, etc.).

2. Prior Art

Except for the present inventors' patent documents, the only publicly-known literature on phosphine oxides having the general formula (2) is the one disclosed by G. N. Koidan et al., in Journal of General Chemistry of the USSR, 55, p1453 (1985).

In this literature, the compound referred to as iminotris(dimethylamino)phosphorane in this patent application, which is iminophosphorane having the general formula (1) whose R is a methyl group, is termed hexamethyltriamidophosphazo hydride and the compound referred to as tris[tris(dimethylamino) phosphoranylidenamino]phosphine oxide in this patent application, which is phosphine oxide having the general formula (2) whose R is a methyl group, is termed tris[tris(N,N-dimethylamido)phosphazo] phosphate.

And the compound referred to as aminotris(dimethylamino)phosphonium chloride in this patent application, which is aminophosphonium chloride having the general formula (3) whose R is a methyl group, is the same as the compound termed hexamethyltriamidophosphazo hydride hydrochloride and shown by the form of [HN=P(NMe$_2$)$_3$].HCl in the above described literature. Hereinafter, for the above described three kinds of compounds the expressions of this application shall be used.

In the above literature, described is the reaction of tris[tris(dimethylamino)phosphoranylidenamino]phosphine oxide with methyl iodide. And a process for preparing tris[tris(dimethylamino)phosphoranylidenamino]phosphine oxide, the raw material of the above reaction, is disclosed.

The literature states that tris[tris(dimethylamino)phosphoranilidenamino]phosphine oxide was obtained in an isolation yield of 85% by, first, adding a solution of phosphorus oxytrichloride in petroleum ether to a solution of iminotris(dimethylamino) phosphorane in petroleum ether drop by drop at 20° C. for 30 minutes while stirring the solution mixture so that the mole ratio of the above described phosphorane to phosphorus oxytrichloride becomes exactly 6:1, after that (the time is not specified), separating the precipitate of aminotris(dimethylamino)phosphonium chloride as a by-product, washing the above described precipitate with petroleum ether, concentrating the filtrate, followed by crystallizing the residue from a small amount of the petroleum ether.

However, when the present inventors carried out the preparation of tris[tris(dimethylamino)phosphoranilidenamino]phosphine oxide under the same conditions as above, even after the addition of phosphorus oxytrichloride at 20° C. for 30 minutes, almost no object compound was produced, as shown in comparative example 5 below. After that, the reaction was proceeded at a raised temperature of 40° C. for 24 hours, however, the reaction yield of an object compound was as low as about 60%. Even after the additional 48 hours of reaction, the reaction yield was about 73% at the most.

In addition, the above literature only states that tris[tris(dimethylamino)phosphoranylidenamino]phosphine oxide was obtained "by crystallizing the residue from a small amount of the petroleum ether", but does not describe in detail the recrystallization process. The present inventors attempted recrystallization of crude phosphine oxide in such a manner that, first precipitate was separated by filtration from the liquid reaction product obtained after the 48 hours' reaction at 40° C., as described above, then the filtrate was concentrated to dry to become a solid.

As shown in comparative example 6 below, a small amount of crystal deposition was observed only after the filtrate was cooled to −10° C., and the crystal could be finally gathered after the filtrate was cooled to an extremely low temperature of −20° C. The isolation yield of the crystal, that is, the isolation yield of tris[tris(dimethylamino)phosphoranylidenamino]phosphine oxide was as low as 20%, and moreover, the crystal contained a large amount of chlorine ion (about 600 ppm). Such residue of chlorine ion is a very serious problem when the above described phosphine oxide is used as a curing catalyst for curing the raw material resin for IC sealing which is required to have an electrical insulating property.

In the case where tris[tris(dimethylamino)phosphoranylidenamino]phosphine oxide is prepared by reacting iminotris(dimethylamino) phosphorane with phosphorus oxytrichloride, if one molecule of iminotris(dimethylamino) phosphorane reacts with one molecule of phosphorus oxytrichloride, one molecule of hydrogen chloride is yield at the same time. This hydrogen chloride immediately reacts with iminotris(dimethylamino) phosphorane to yield ionic aminotris(dimethylamino)phosphonium chloride. Accordingly, 6 moles of iminotris(dimethylamino) phosphorane is required stoichiometrically so as to react all of the three chlorines of one mole of phosphorus oxytrichloride. This is expressed by the following reaction equation.

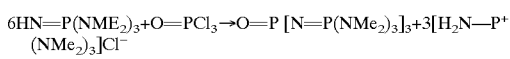

6HN=P(NME$_2$)$_3$+O=PCl$_3$→O=P [N=P(NMe$_2$)$_3$]$_3$+3[H$_2$N—P$^+$(NMe$_2$)$_3$]Cl$^-$

As shown in comparative example 7 below, in the purifying process described in the above described literature, when imino(dimethylamino) phosphorane was used in excess of that stoichiometrically required so as to increase yields, the unreacted residue of the above described phosphorane could not be removed sufficiently, which led to a decrease in purity of recrystallized tris[tris(dimethylamino)phosphoranylidenamino]phosphine oxide.

Thus, the above disclosed process for preparing tris[tris(dimethylamino)phosphoranylidenamino]phosphine oxide is still very insufficient as an industrial process in that: its reaction and isolation yields are low, the purification process for its product requires an extremely low temperature, the ionic compound yielded by its reaction cannot be removed sufficiently, and its unreacted raw material cannot be removed sufficiently when using one reactant in excess of that stoichiometrically required in order to increase yields.

SUMMARY OF THE INVENTION

Accordingly, it is a primary object of the present invention to provide a process for preparing phosphine oxides having the general formula (2) in a raised yield which comprises reacting iminophosphoranes having the general formula (1) with phosphorus oxytrichloride.

Another object of the present invention is to provide a process for purifying the above described phosphine oxides which makes it possible in an industrially more realistic manner to remove unreacted raw materials and ionic impurities in a liquid reaction product and to provide a high yield and purity of the above described phosphine oxides.

After continuously concentrating their energies on investigating processes for preparing and purifying the above described phosphine oxides so as to achieve the above objects, the present inventors finally found that in the process for preparing phosphine oxides having the general formula (2) which comprises reacting iminophosphoranes having the general formula (1) with phosphorus oxytrichloride, the use of an aprotic organic solvent with permittivity 2.2 or more at 20° C. instead of petroleum ether (with permittivity 1.85 to 1.95 at 20C.), as a reaction solvent, increases the reaction rate remarkably and gives the above described phosphine oxides in a high yield.

In addition, it was found that, although one part by weight of petroleum ether is a good solvent to dissolve 1.5 parts by weight or more of the above described phosphine oxides, when the liquid reaction product reacted in a petroleum ether as a reaction solvent is washed with a small amount of water, almost all amount of the above described phosphine oxides moves to a water phase and there is almost none left in a petroleum ether phase.

Surprisingly, however, it was found that in a liquid reaction product obtained by using a specific solvent, such as o-dichlorobenzene, almost all amount of the above described phosphine oxides is left in an organic phase even after water-washing and almost all amount of the aminophosphonium chlorides having the general formula (3) which are yielded by the reaction and the unknown compounds as by-products move to a water phase, as shown in example 8 below. Further surprisingly, it was also found that, when iminophosphoranes are used in a stoichiometrically required amount or in excess of the same amount, almost all amount of the iminophosphoranes having the general formula (1) which are left unreacted in the liquid reaction product move to a water phase.

As described above, the present inventors found that the use of an aprotic organic solvent with permittivity 2.2 or more at 20° C. as a reaction solvent is effective in increasing the reaction rate as well as the reaction yield, as a result, producing the phosphine oxides having the general formula (2) in a high yield, and in increasing the purity of the above described phosphine oxides simply by water-washing the solution containing the above described phosphine oxides and a specific organic solvent while keeping the isolation yield almost the same. Thus the present invention was completed.

Accordingly, the first aspect of the present invention is a process for preparing phosphine oxides having the following general formula (2):

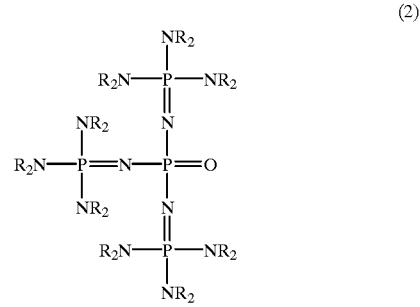

wherein R represents the same kind or different kinds of hydrocarbon group(s) with 1 to 10 carbon atom(s), and two Rs on the same nitrogen atom can combine with each other to form a ring structure, which comprises reacting iminophosphoranes having the following general formula (1):

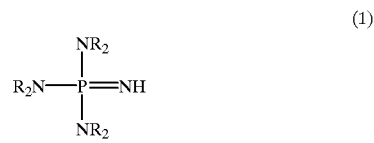

wherein R is the same as that of the formula (2), with phosphorus oxytrichloride, in the presence of an aprotic organic solvent with permittivity 2.2 or more at 20° C. as a reaction solvent.

The second aspect of the present invention is a process for purifying phosphine oxides which comprises water-washing a solution containing at least phosphine oxides having the general formula (2) and an organic solvent which does not substantially mix with water to give the above described phosphine oxides as a solution, or concentrating to dry the above described solution to give the above described phosphine oxides as a solid.

DETAILED DESCRIPTION OF THE INVENTION

In the preparation and purification processes of the present invention, the chemical structure of phosphine oxides is expressed by the general formula (2); however, the formula just expresses one canonical structure. According to the formula (2), a double bond is formed between phosphorus atom and oxygen atom; however, phosphine oxides may have another canonical structure where electrons cluster on the side of oxygen atom to form an anion of oxygen and a cation of phosphorus ($P^+$—$O^-$). The cation of phosphorus may be delocalized through a conjugated system. It should be understood that phosphine oxides having the formula (2) in the preparation and purification processes of the present invention are resonance hybrids including all of the above described structure.

In the preparation and purification processes of he present invention, R of iminophosphoranes having the general formula (1), of phosphine oxides having the formula (2) and of aminophosphonium chlorides having the formula (3) represents the same kind of or different kinds of hydrocarbon group(s) with 1 to 10 carbon atom(s). In particular, the R represents an aliphatic or aromatic hydrocarbon group such as methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (commonly known as tert-octyl), nonyl, decyl, phenyl, 4-toluyl, benzyl, 1-phenylethyl, or 2-phenylethyl.

When two Rs on the same nitrogen atom of iminophosphoranes having the general formula (1), of phosphine oxides having the formula (2) and of aminophosphonium chlorides having the formula (3) combine with each other to form a ring structure together with the nitrogen atom, the formed cyclic amino groups are cyclic secondary amino groups containing 4 to 6 carbon toms on the ring, and —NR$_2$'s are cyclic secondary amino groups of 5 to 7 members including a nitrogen atom.

The above described cyclic secondary amino groups include, for example, pyrrolidine-1-yl group, piperidine-1-yl group, morpholine-4-yl group, and substitution products thereof substituted with alkyl groups such as methyl group and ethyl group.

All of or part of the potential nitrogen atoms of the above described iminophosphoranes, phosphine oxides and aminophosphonium may participate in the formation of such a ring structure.

R is preferably an aliphatic hydrocarbon group with 1 to 8 carbon atoms, such as methyl, ethyl, n-propyl, isopropyl, tert-butyl, tert-pentyl, or 1,1-dimethyl-3,3-dimethylbutyl, and more preferably a methyl group.

The above described iminophosphoranes having the general formula (1) can be synthesized in the same manner as the description in EP-0921128 or G. N. Koidan et al., Zh. Obshch. Khim., 50, 679–680 (1980). Of the above described iminophosphoranes, the one whose R is a methyl group is commercially available.

The first aspect of the present invention is a process for preparing phosphine oxides having the formula (2) which comprises reacting iminophosphoranes having the general formula (1) with phosphorus oxytrichloride, wherein an aprotic organic solvent with permittivity 2.2 or more at 20° C. is used as a reaction solvent.

The preparation process of the present invention is characterized by use of an aprotic organic solvent with permittivity 2.2 or more at 20° C. as a reaction solvent. The use of an aprotic organic solvent with permittivity less than 2.2 at 20° C. as a reaction solvent causes an extreme decrease in reaction rate under the same mild conditions. On the other hand, if the reaction temperature is raised so as to increase the reaction rate, a side reaction proceeds, as a result of which phosphine oxides having the general formula (2) cannot be obtained in a high yield.

The aprotic organic solvents with permittivity less than 2.2 at 20° C. include, for example, petroleum ether (1.85 to 1.95; permittivity at 20° C. and so on), hexane (1.89), decane (1.99), 1-hexene(2.06), 1-octene (2.08), cyclohexane (2.05) and decalin (2.19), all of which are not preferable as a reaction solvent of the present invention.

Concrete examples of the aprotic organic solvents with permittivity 2.2 or more at 20° C. used in the preparation process of the present invention as a reaction solvent include, for example, halogenated aliphatic hydrocarbons such as methylene chloride, chloroform, 1,2-dichloroethane, 1,1-dichloroethane or hexachloroethane; aromatic hydrocarbons such as benzene, toluene, o-xylene, m-xylene, p-xylene, mixed xylene, ethylbenzene, normal propylbenzene, cumene, 1,2,3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene; ethers such as diethyl ether, dipropyl ether, diisopropyl ether, dibutyl ether, dimethoxyethane, diethylene glycol dimethyl ether, tetrahydrofuran, tetrahydropyran, 1,4-dioxane, anisole or phenetol; esters such as methyl formate, ethyl formate, propyl formate, isobutyl formate, methyl acetate, ethyl acetate, propyl acetate, butyl acetate, methyl propionate, ethyl propionate, methyl butyrate, methyl benzoate, isopentyl benzoate or ethyl cinnamate; nitro compounds such as nitromethane, nitroethane or nitrobenzene; and polar compounds such as acetonitrile, propionitrile, benzonitrile, N,N-dimethylformamide, N-methylpyrrolidone, dimethyl sulfoxide or hexamethylphosphorictriamide. For further details, refer to Teruzo Asahara et al. Handbook of Solvents (Tokyo: Kodansha Publishing Company, 1982).

Any other aprotic organic solvents may be used, as long as their permittivity is 2.2 or more at 20° C. and they do not hinder the preparation process of the present invention. These aprotic organic solvents may be used independently or jointly. Further, the aprotic organic solvent system which is a mixture of the above described aprotic organic solvents and the aprotic organic solvents with permittivity less than 2.2 at 20° C. and allowed to have permittivity of 2.2 or more at 20° C. should be understood as an "aprotic organic solvent with permittivity 2.2 or more at 20° C." in the preparing process of the present invention.

Of these aprotic organic solvents, preferable are those which do not dissolve aminophosphonium chlorides having the formula (3) described below. The preferable aprotic organic solvents include, for example, aromatic hydrocarbons such as benzene, toluene, o-xylene, m-xylene, p-xylene, mixed xylene, ethylbenzene, normal propylbenzene, cumene, 1,2,3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene; and ethers such as diethyl ether, dipropyl ether, diisopropyl ether, dibutyl ether, dimethoxyethane, diethylene glycol dimethyl ether, tetrahydrofuran, tetrahydropyran, 1,4-dioxane, anisole or phenetol.

Of the above described aprotic organic solvents, more preferable are those substantially immiscible with water as described in the purification process of the present invention. The aprotic organic solvents substantially immiscible with water include, for example, aromatic hydrocarbons such as benzene, toluene, o-xylene, m-xylene, p-xylene, mixed xylene, ethylbenzene, normal propylbenzene, cumene, 1,2,3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; and halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene. And more preferable are toluene, chlorobenzene, dichlorobenzene or 2,4-dichlorotoluene.

The amount of these aprotic organic solvents used is not expressly restricted; however, it is normally 500 weight parts or less per 1 weight part of phosphorus oxytrichloride as a raw material, preferably 1 to 100 weight parts, and more preferably 1.5 to 50 weight parts. It is not a problem that part of the liquid phosphorus oxytrichloride can be immiscible with these aprotic organic solvents.

In the preparation process of the present invention, the mole ratio of iminophosphoranes having the formula (1) used to phosphorus oxytrichloride is not expressly restricted; however, it is normally 5 to 12, preferably 6 to 10, and more preferably 6.1 to 8.0.

The reaction temperature varies depending on the amount of solvent used, on the mole ratio of the raw materials, etc.; however, it is normally −10 to 200° C., preferably 0 to 150° C., and more preferably 15 to 100° C. In the reaction, the set temperature may be changed phase by phase; for example, the reaction may be carried out at a relatively low temperature in the beginning and at a relatively high temperature in the last.

The reaction may be carried out under reduced pressure, under normal pressure and under pressure; however, it is normally carried out under normal pressure. The reaction time varies depending on the reaction temperature and other factors; however, it is normally 0.1 to 100 hours, preferably 0.5 to 50 hours, and more preferably 1 to 30 hours.

In the liquid reaction product thus obtained, aminophosphonium chlorides having the formula (3) can sometimes be deposited as a solid and can sometimes be dissolved depending on the kind or amount of the solvent used or on the kind of iminophosphoranes having the formula (1). The methods of removing the above described phosphonium chlorides in such states are not restricted to specific ones and any methods can be used to remove them; however, when the above described phosphonium chlorides are deposited in the liquid reaction product as a solid, the method in which the liquid reaction product directly undergoes a solid-liquid separation is normally used; and when the above described phosphonium chlorides are dissolved in the liquid reaction product, first the solvent used is distilled from the liquid, then another organic solvent which does not dissolve the above described phosphonium chlorides is added, and the liquid reaction product can undergo a solid-liquid separation.

The above solid-liquid separation can be conducted using any methods; however, general-purpose methods such as filtration, centrifugation and decantation are normally used. Of the above methods, filtration is most preferable. If needed, filter cake can be washed with the above described aprotic organic solvent or an organic solvent which does not dissolve the above described phosphonium chlorides, and the washings may be added to the filtrate.

The organic solvents which do not dissolve the above described phosphonium chlorides include, for example, saturated aliphatic hydrocarbons such as normal pentane, normal hexane, 2,2-dimethylbutane, 2,3-dimethylbutane, 2-methylpentane, normal heptane, normal octane, 2,3,3-trimethylpentane, isooctane, normal nonane, 2,2,5-trimethylhexane or normal decane; alicyclic hydrocarbons such as cyclopentane, methylcyclopentane, cyclohexane, methylcyclohexane, ethylcyclohexane, p-menthane, bicyclohexyl or decalin; aromatic hydrocarbons such as benzene, toluene, o-xylene, m-xylene, p-xylene, mixed xylene, ethylbenzene, normal propylbenzene, cumene, 1,2,3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene; and ethers such as diethyl ether, dipropyl ether, diisopropyl ether, dibutyl ether, dimethoxyethane, diethylene glycol dimethyl ether, tetrahydrofuran, tetrahydropyran, 1,4-dioxane, anisole or phenetol. The organic solvents which do not dissolve the above described phosphonium chlorides are, however, limited to the above described ones.

The above described phosphonium chlorides separated as solids can be re-formed as iminophosphoranes having the formula (1) by the method described in EP-0921128 or G. N. Koidan et al., Zh. Obshch. Khim., 50, 679–680 (1980) and recycled as part or the whole of the iminophosphoranes having the formula (1) in the preparation process of the present invention.

In the mother liquor from which the aminophosphonium chlorides having the formula (3) have been removed, there exist iminophosphoranes having the formula (1) which remain unreacted or are added in excess. The methods of removing the above described phosphoranes are not restricted to specific ones and any methods can be used to remove them; however, normally used are the method in which the above described mother liquor is concentrated to dry and the above described phosphoranes are distilled off under normal pressure or under reduced pressure and the method in which the above described mother liquor is washed with water as described below.

The dried solid and the solution having undergone water washing thus obtained contain phosphine oxides having the formula (2) of a sufficiently high purity. Although they can sometimes be used as they are for next purpose, they can sometimes be used as a concentrated solution or a solid by removing a small amount of water contained therein with a drying agent or by distillation or, in case of solutions having undergone the above described water washing, by removing part of or the whole solvent used.

The second aspect of the present invention is a process for purifying phosphine oxides having the formula (2) which comprises water washing a solution containing at least the above described phosphine oxides and an organic solvent substantially immiscible with water to give the above described phosphine oxides as a solution, or further comprises concentrating to dry the above described solution to give the above described phosphine oxides as a solid. "The organic solvents substantially immiscible with water" used in the purification process of the present invention mean organic solvents conventionally used for extraction etc. which dissolve in water too little to be taken into consideration and can be easily separated from water phase. In addition, the partition rate of their phase to water phase is high in terms of phosphine oxides having the formula (2), and they cause no chemical process even if they come in contact with the above described phosphine oxides. The organic solvents substantially immiscible with water as described above include, for example, halogenated aliphatic hydrocarbons such as methylene chloride, chloroform, 1,2-dichloroethane, 1,1-dichloroethane or hexachloroethane;

aromatic hydrocarbons such as benzene, toluene, o-xylene, m-xylene, p-xylene, mixed xylene, ethylbenzene, normal propylbenzene, cumene, 1,2,3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene; and esters having 4 or more of carbon atoms such as propyl formate, isobutyl formate, ethyl acetate, propyl acetate, butyl acetate, methyl propionate, ethyl propionate, methyl butylate, methyl benzoate, isopentyl benzoate or ethyl cinnamate. Any other organic solvents may be used, as long as they do not hinder the purification process of the present invention.

Of the above described organic solvents, preferable are aprotic organic solvents with permittivity 2.2 or more at 20° C. which do not dissolve aminophosphonium chlorides having the formula (3). The preferable aprotic organic solvents include, for example, aromatic hydrocarbons such as benzene, toluene, o-xylene, m-xylene, p-xylene, mixed xylene, ethylbenzene, normal propylbenzene, cumene, 1,2, 3-trimethylbenzene, 1,2,4-trimethylbenzene, mesitylene, tetralin, butylbenzene, p-cymene, cyclohexylbenzene, 1,4-diethylbenzene, 1,3-diisopropylbenzene or dodecylbenzene; and halogenated aromatic hydrocarbons such as chlorobenzene, o-dichlorobenzene, m-dichlorobenzene, bromobenzene, o-dibromobenzene, 1-bromo-2-chlorobenzene, 1-bromonaphthalene, 1-chloronaphthalene, 2-chlorotoluene, 2-bromotoluene, 2,4-dichlorotoluene, 1-bromo-2-ethylbenzene, 2-chloro-o-xylene or 1,2,4-trichlorobenzene. More preferable are toluene, chlorobenzene or o-dichlorobenzene.

"A solution containing at least phosphine oxides having the formula (2) and an organic solvent substantially immiscible with water" used in the purification process of the present invention means a solution containing at least the above described two components, and there may exist other components in the solution, as long as they do not hinder the purification process of the present invention. Further, the solution may be a solution formed by dissolving the above described phosphine oxides, which was once separated from another solution, in an organic solvent substantially immiscible with water.

Further, the solution may be a solution formed by removing solid aminophosphonium chlorides having the formula (3) from a liquid reaction product containing phosphine oxides having the formula (2) and the above described aminophosphonium chlorides by the solid-liquid separation process, wherein the liquid reaction product is formed by reacting iminophosphoranes having the formula (1) with phosphorus oxytrichloride using as a reaction solvent an aprotic organic solvent with permittivity 2.2 or more at 20° C. which is substantially immiscible with water and does not dissolve the aminophosphonium chlorides having the formula (3), the above described phosphine oxides and phosphonium chlorides being yielded at the same time by the above described reaction. According to the situations, the solution may be a solution formed in such a manner that, first the above described reaction is carried out using an aprotic organic solvent with permittivity 2.2 or more at 20° C. as a reaction solvent, then the above described solvent is removed by, for example, the method of distilling solvent from the solution obtained by the solid-liquid separation process, which is described in the preparation process of the present invention, finally another desired organic solvent substantially immiscible with water is added instead of the above described solvent removed.

Of the above described solutions, preferable is a solution formed by removing solid aminophosphonium chlorides having the formula (3) from a liquid reaction product containing phosphine oxides having the formula (2) and the above described aminophosphonium chlorides by the solid-liquid separation process, wherein the liquid reaction product is formed by reacting iminophosphoranes having the formula (1) with phosphorus oxytrichloride using as a reaction solvent an aprotic organic solvent with permittivity 2.2 or more at 20° C. which is substantially immiscible with water and does not dissolve the aminophosphonium chlorides having the formula (3), the above described phosphine oxides and phosphonium chlorides being yielded at the same time by the above described reaction. And more preferable is a solution formed by removing the above described phosphonium chlorides from a liquid reaction product containing the same by the solid-liquid separation process, wherein the liquid reaction product is formed by reacting the above described phosphoranes with phosphorus oxytrichloride at the above described phosphoranes to phosphorus oxytrichloride mole ratio within 6 to 10.

As a method of water washing in the purification process of the present invention, any method can be used as long as the method allows the solution containing at least phosphine oxides having the formula (2) and an organic solvent substantially immiscible with water and water to sufficiently come in contact with each other. Usually water washing can be carried out in such a manner that first water is added to the above described solution, the solution is fully stirred, and its water phase is removed after its organic phase and water phase are separated from each other.

The amount of water used for the water washing is not expressly restricted; however, 5 weight parts or less of water is usually used per 1 weight part of the above described solution. The water washing can be carried out using such an amount of water in several installments. Preferably the water washing is carried out 2 to 5 times using 0.05 to 1.0 weight parts of water at a time per 1 weight part of the above described solution. The temperature and duration of water washing are not expressly restricted; however, the temperature is usually 10 to 80° C., preferably 15 to 40° C., and the duration is usually within 3 hours, preferably 0.01 to 1 hour, more preferably 0.05 to 0.5 hours.

A solution of phosphine oxides having the formula (2) which has been subjected to water washing in the above manner contains the above described phosphine oxides of a higher purity, and it can sometimes be used as it is for the next purpose. The above described phosphine oxides can be obtained as solids by concentrating to dry the solution.

According to situations, the dried solids can be further purified. The solvent used may be completely removed from the dried solids, or it may remain in the solids in a small amount. There exist a trace of impurities left dissolved in such solids even after water washing. The methods of further purifying such solids are not expressly restricted; however, a method in which one of hydrocarbons is added to the dried solids so as to dissolve phosphine oxides having the formula (2) and a trace of solids (impurities) left undissolved are removed by the solid-liquid separation process is preferable, effective and practical.

Hydrocarbons used in this method include, for example, saturated aliphatic hydrocarbons such as normal pentane, normal hexane, 2,2-dimethylbutane, 2,3-dimethylbutane, 2-methylpentane, normal heptane, normal octane, 2,3,3-trimethylpentane, isooctane, normal nonane, 2,2,5-trimethylhexane or normal decane; alicyclic hydrocarbons such as cyclopentane, methylcyclopentane, cyclohexane, methylcyclohexane, ethylcyclohexane, p-menthane, bicyclohexyl or decalin; and aromatic hydrocarbons such as benzene, toluene, o-xylene, m-xylene or p-xylene.

Any other hydrocarbons may be used as long as they do not hinder this method. These hydrocarbons may be used independently or jointly. Of the above described hydrocarbons, preferable are saturated aliphatic hydrocarbons having 5 to 10 carbon atoms, such as normal pentane, normal hexane, normal heptane, normal octane, normal nonane or normal decane.

The amount of these hydrocarbons used is not expressly restricted; however, usually used are hydrocarbons 0.5 to 50 times as heavy as the above described dried solids, preferably hydrocarbons 1 to 20 times as heavy as the above described dried solids. When hydrocarbons are added to the above described dried solid to dissolve phosphine oxides having the formula (2), the temperature and duration in the above operation are not expressly restricted; however, the temperature is usually 10 to 100° C., preferably 20 to 50° C., the duration is usually 0.1 to 3 hours, preferably 0.5 to 2 hours. After that, the solid left undissolved in the above described hydrocarbon solution is removed by the solid-liquid separation process. The solid-liquid separation can be conducted using any methods; however, general-purpose methods such as filtration, centrifugation and decantation are usually used. Of the above methods, filtration is most preferable. The undissolved solid can be washed with hydrocarbons, and the washings may be combined to the filtrate.

Thus, a solution containing phosphine oxides having the formula (2) of a extremely high purity can be obtained. If needed, the above described solution can be concentrated to dry to obtain the above described phosphine oxides as a solid.

The present invention will be further illustrated by the following examples; however, these examples are intended to illustrate the invention and are not intended to limit the invention to the specific examples.

EXAMPLE 1

Under a nitrogen atmosphere, 54.3 g (305 mmol) of iminotris(dimethylamino) phosphorane, which is iminophosphorane having the formula (1) whose R is a methyl group, and 130 g of dried o-dichlorobenzene (with permittivity 6.80 at 20° C.) were prepared in a 300 ml glass reactor vessel. Then, a liquid mixture of 7.67 g (50.0 mmol) of phosphorus oxytrichloride and 16.3 g of dried o-dichlorobenzene (the concentration of phosphorus oxytrichloride was 32 weight %) was added drop by drop over 30 minutes while stirring the mixture and controlling the internal temperature to be kept at 20° C. The mole ratio of iminotris(dimethylamino)phosphorane to phosphorus oxytrichloride was 6.1. At this time, part of the liquid reaction product was taken as a sample.

A $^{31}$P-NMR quantitative analysis was conducted using dimethyl sulfoxide deuteride as a solvent and tri-normal-butyl phosphate as an internal standard compound (hereafter, yield and purity were analyzed in this manner). The analysis shows that almost no tris[tris(dimethylamino) phosphoranylidenamino]phosphine oxide, which is phosphine oxide having the formula (2) whose R is a methyl group, was formed. Then, the temperature of the liquid reaction product was raised to 40° C. and the reaction was continued for 24 hours, as a result of which the above described phosphine oxide was obtained in a reaction yield to phosphorus oxytrichloride of 83.6%.

This result, together with the results of examples 2 to 7 and comparative examples 1 to 4 where reaction was carried out using respective solvents other than o-dichlorobenzene whose permittivity is 2.2 or more or less than 2.2 at 20° C., is shown in Table 1. Table 1 shows that there existed a big clear difference in reaction rate between the solvents with permittivity 2.2 or more at 20° C. and with permittivity less than 2.2 at 20° C.,in addition, the use of the solvents with permittivity 2.2 or more at 20° C. is very effective in increasing the reaction yield of the object compound.

EXAMPLES 2–7

Comparative Examples 1–4

The reaction was carried out exactly in the same manner as example 1, except that various types aprotic organic solvents shown in Table 1 were used instead of o-dichlorobenzene.

TABLE 1

| Examples | Aprotic Organic Solvent | Permittivity | Reaction Yield (%) |
|---|---|---|---|
| Example 2 | Benzene | 2.28 | 81.9 |
| Example 3 | Chloroform | 4.81 | 81.3 |
| Example 4 | Ethyl Acetate | 6.08 | 85.4 |
| Example 1 | o-Dichlorobenzene | 6.80 | 83.6 |
| Example 5 | Tetrahydrofuran | 7.60 | 89.7 |
| Example 6 | Nitrobenzene | 34.9 | 92.2 |
| Example 7 | Acetonitrile | 37.5 | 91.6 |
| Comparative Example 1 | Hexane | 1.89 | 55.6 |
| Comparative Example 2 | Petroleum Ether | 1.85–1.95 | 58.1 |
| Comparative Example 3 | 1-Hexene | 2.06 | 57.5 |
| Comparative Example 4 | Decalin | 2.19 | 51.9 |

Note: Permittivity represents permittivity at 20° C.

EXAMPLE 8

Under a nitrogen atmosphere, 15.4 g (100 mmol) of phosphorus oxytrichloride and 154 g of dried o-dichlorobenzene were prepared in a 500 ml glass reactor vessel. Then, 116 g (651 mmol) of iminotris (dimethylamino) phosphorane was added drop by drop over 1 hour while stirring the mixture and controlling the bulk temperature to be kept at 70° C. or lower. The mole ratio of iminotris(dimethylamino)phosphorane to phosphorus oxytrichloride was 6.5. After completing the addition of iminotris(dimethylamino)phosphorane, stirring was continued at 70° C. for 1 hour, so as to obtain a white slurry. Part of this liquid reaction product was taken as a sample and a quantitative analysis was conducted. The analysis shows that the reaction yield of tris[tris(dimethylamino) phosphoranylidenamino]phosphine oxide was 85.4%.

After the reaction, the above described white slurry was filtered, the solid was washed with a small amount of o-dichlorobenzene, and 266 g of filtrate and washings was obtained. The filtrate and washings was taken in a 300 ml separating funnel, 31.9 g of water (0.12 times as heavy as the filtrate and washings) was added, and water-washing was conducted of the filtrate and washings while intensely shaking the separating funnel so that both of the o-dichlorobenzene phase and the water phase were satisfactorily contacted with each other, then the separating funnel was allowed to stand still to separate the o-dichlorobenzene phase and the water phase from each other, and each phase was collected as a sample. This water-washing operation was carried out another two times.

A quantitative analysis was conducted of the o-dichlorobenzene phase obtained, and the analysis shows that iminotris(dimethylamino)phosphorane, which was left unreacted before water-washing, was decreased to an amount less than the limit of detection and the amount of by-products was also drastically decreased compared with that before water-washing. Then, the o-dichlorobenzene phase was concentrated to dry at 80° C., 10 mmHg to obtain 50.5 g of white solid.

The purity of tris[tris(dimethylamino) phosphoranylidenamino]phosphine oxide in the solid was 95.4 weight % and the isolation yield was 83.3%. As described above, the above described phosphine oxide was obtained with little loss and with a satisfactorily high purity only by water-washing the filtrate and washings after filtrating the liquid reaction product.

In order to further purify the above described phosphine oxide, the obtained solid was dissolved in normal hexane which was 10 times as heavy as the solid while stirring the solution over 40 minutes. After that, the solid left undissolved was filtered, and the undissolved matter was washed with a small amount of normal hexane. The undissolved solid was about 1.9 g in weight after being dried. The filtrate and washings obtained was concentrated to dry at 60° C., 10 mmHG and subjected to drying operation at 80° C. for 5 hours under the flow of nitrogen.

As a result, 48.5 g of white solid was obtained, and its isolation yield was 83.1% and its purity was increased to as high as 99.2 weight %. Then, the chlorine ion content of the solid was measured by the potentiometric titration method using a chlorine ion electrode (hereafter the same as above). The measured value was 43 ppm.

Comparative Example 5

The reaction was carried out in accordance with the process described in the literature by G. N. Koidan et al.

Under a nitrogen atmosphere, 53.5 g (300 mmol) of iminotris(dimethylamino) phosphorane and 200 ml of dried petroleum ether were prepared in a 300 ml glass reactor vessel (the concentration of the above described phosphorane was 29 weight %). Then, a liquid mixture of 7.67 g (50.0 mmol) of phosphorus oxytrichloride and 25 ml of dried petroleum ether (the concentration of phosphorus oxytrichloride was 32 weight %) was added drop by drop over 30 minutes while stirring the mixture and controlling the bulk temperature to be kept at 20° C.

The mole ratio of iminotris(dimethylamino)phosphorane to phosphorus oxytrichloride was 6.0. At this time, part of the liquid reaction product was taken as a sample, and it was found that almost no object compound was formed. Then, the liquid reaction product was heated at its ref lux temperature (about 40° C.) and the reaction was continued. The yields after 24 hours and 48 hours were 59.8% and 73.0%, respectively. As is apparent when compared with the results of examples 1 to 7, in the process in accordance with the description in the above described literature, both reaction rate and yield were low.

Comparative Example 6

Purification was carried out using the liquid reaction product obtained in accordance with the process described in the literature by G. N. Koidan et al. (the liquid reaction product obtained in comparative example 5) in accordance with the purification process described in the above described literature.

The white slurry of petroleum ether obtained from the reaction in comparative example 5 was filtered, the solid left after the filtration was washed twice with 50 ml of petroleum ether, and the obtained filtrate and washings was concentrated to dry at 30° C., 150 mmHg. As a result, 21.5 g of faintly yellowish white solid was obtained. When 6.0 g of petroleum ether (only 28 weight % of the solid) was added, the solid was almost completely dissolved in the petroleum ether at 25°C. The solution thus obtained was filtered, and the filtrate was cooled so as to crystallize. However, a very small amount of crystallization was observed only after the temperature of the filtrate was reduced to −10°C.

The filtrate temperature was further reduced to −20°C., and a certain amount of crystallization was finally achieved. The filtrate thus obtained was immediately filtered by using a cold filtration system at −20° C., the filtered crystal was washed with about 3 g of petroleum ether cooled at −30° C., and 5.89 g of white crystal was obtained. This crystal was tris[tris(dimethylamino)phosphoranylidenamino]phosphine oxide with purity 98.2 weight %; however, the yield was only 20.0% and the concentration of chlorine ion was as high as 640 ppm.

As described above, even though recrystallization was carried out using a small amount of solvent, an extremely low temperature was required; and moreover, the yield of crystal was very low.

Comparative Example 7

The reaction was carried out exactly in the same manner as comparative example 5, except that the amount of iminotris(dimethylamino)phosphorane used was 57.9 g (325 mmol) and the reaction time at the reflux temperature of the liquid reaction product (about 40° C.) was 30 hours. And the purification was carried out at −20° C. exactly in the same manner as comparative example 6. The mole ratio of iminotris(dimethylamino)phosphorane to phosphorus oxytrichloride was 6.5 (in excess of that stoichiometrically required). The yield after the reaction was 75.3%, and apparently the reaction rate was increased compared with the result of comparative example 5 only because the amount of the above described phosphorane used was increased.

After the recrystallization, 6.57 g of white crystal was obtained. The purity of the crystal was 94.1 weight % and the yield was 20.7%. Even after the operation of recrystallization, the purity was not satisfactory. In the crystal, about 2 weight % of iminotris(dimethylamino) phosphorane as well as unknown impurities was observed. The above described phosphorane used in excess of that stoichiometrically required in the reaction could not be fully removed by this process, as a result, it remained in the object crystal deposited after the operation of recrystallization.

Comparative Example 8

The reaction was carried out exactly in the same manner as comparative example 5, except that the reaction time at the reflux temperature of the liquid reaction product (about 40° C.) was 40 hours. The yield after the reaction was 70.2%. The white slurry of petroleum ether obtained was filtered, and the solid was washed twice with 50 ml of petroleum ether. To the filtrate and washings obtained, water 0.12 times as heavy as the filtrate was added, and water-washing was conducted of the filtrate and washings while intensely shaking the mixed solution so that both of the petroleum ether phase and the water phase were satisfactorily contacted with each other, then the mixed solution was allowed to stand still to separate the petroleum ether phase and the water phase from each other, and each phase was collected as a sample. This water-washing operation was carried out another two times.

When a quantitative analysis was conducted of the petroleum ether phase obtained, it was revealed that almost no object compound, that is, tris[tris-(dimethylamino) phosphoranylidenamino]phosphine was contained in the petroleum ether phase. Then, the same analysis was conducted of the water phase. The analysis revealed that 99 weight % of the object compound contained before water washing, together with by-products and iminotris (dimethylamino)phosphorane left unreacted, was contained in the water phase.

EXAMPLE 9

The reaction and the water washing were carried out in the same manner as example 8, except that dried toluene was used instead of o-dichlorobenzene. The toluene phase obtained after the water washing was concentrated to dry at 60° C., 50 mmHg. The solid obtained was the object compound with purity 93.5 weight %, and its yield was 82.9%.

EXAMPLE 10

The reaction and the water washing were carried out in the same manner as example 8, except that dried 2,4-dichlorotoluene was used instead of o-dichlorobenzene. The 2,4-dichlorotoluene phase obtained after the water washing was concentrated to dry at 90° C., 10 mmHg. The solid obtained was the object compound with purity 96.1 weight%, and its yield was 82.4%.

EXAMPLE 11

The reaction and the water washing were carried out in the same manner as example 8, except that dried chlorobenzene was used instead of o-dichlorobenzene, that the amount of iminotris(dimethylamino)phosphorane used was 112 g (628 mmol), of that the bulk temperature at the time of dropping the above described phosphorane was controlled to be kept at 60° C. or lower and that the reaction temperature after the dropping was 60° C. The mole ratio of iminotris (dimethylamino)phosphorane to phosphorus oxytrichloride was 6.3. The chlorobenzene phase obtained after the water washing was concentrated to dry at 80° C., 60 mmHg. The solid obtained was the object compound with purity 94.1 weight %, and its yield was 67.3%.

EXAMPLE 12

The reaction and the water washing were carried out in the same manner as example 11, except that the amount of iminotris(dimethylamino)phosphorane used was 120 g (673 mmol). The mole ratio of iminotris(dimethylamino) phosphorane to phosphorus oxytrichloride was 6.7. The solid obtained by concentrating to dry the chlorobenzene phase after the water washing was the object compound with purity 95.9 weight %, and its yield was 80.7%.

EXAMPLES 13, 14

The solid obtained by concentrating to dry o-dichlorobenzene phase, which was obtained by carrying out the reaction and the water washing exactly in the same manner as example 8, was purified in the same manner as example 8, except that normal heptane 15 times as heavy as normal hexane used in example 8 (example 13) and normal octane twice as heavy as normal hexane used in example 8 (example 14) were used. The yields of the object compound obtained were 83%, almost the same in both cases, and the purities were 98.9 weight % and 97.6 weight % in the order described above.

EXAMPLE 15

The reaction and the water washing were carried out exactly in the same manner as example 8, except that the amount of the water used at a time was 0.20 times as heavy as the filtrate and washings. The solid obtained by concentrating to dry o-dichlorobenzene phase after the water washing was the object compound with purity 96.5 weight %, and its yield was 79.9%.

As described above, according to the present invention, in the process for preparing phosphine oxides having the formula (2) which comprises reacting iminophosphoranes having the formula (1) with phosphorus oxytrichloride, purification can be carried out in a simpler and easier way, the above described phosphoranes can be used in excess of that stoichiometrically required, and the above described phosphine oxides can be obtained with higher purity and in a higher yield in an industrially more realistic way.

What is claimed is:

1. A process for preparing phosphine oxides having the following formula (2):

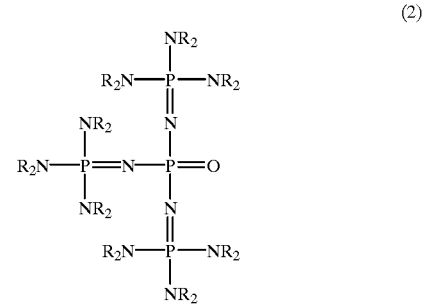

(2)

wherein R represents the same kind of or different kinds of hydrocarbon group(s) with 1 to 10 carbon atoms, and two Rs on the same nitrogen atom can combine with each other to form a ring structure, which comprises reacting iminophosphoranes having the following formula (1):

(1)

wherein R is the same as that of the formula (2), with phosphorus oxytrichloride, in the presence of an aprotic organic solvent with permittivity 2.2 or more at 20° C. as a reaction solvent.

2. The process for preparing phosphine oxides according to claim 1, wherein R of said iminophosphoranes having the formula (1) and of said phosphine oxides having the formula (2) is a methyl group.

3. The process for preparing phosphine oxides according to claim 2, wherein said aprotic organic solvent does not dissolve aminophosphonium chlorides having the following formula (3):

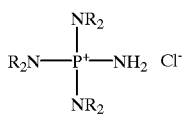

(3)

wherein R is the same as that of the formulae (1) and (2).

4. The process for preparing phosphine oxides according to claim 2, wherein said aprotic organic solvent does not dissolve aminophosphonium chlorides having the formula (3) and is substantially immiscible with water wherein formula (3) is as follows:

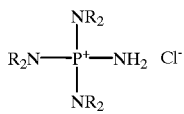

(3)

wherein R is the same as that of the formulae (1) and (2).

5. The process for preparing phosphine oxides according to claim 4, wherein the number of moles of said iminophosphoranes having the formula (1) used per 1 mole of phosphorus oxytrichloride is in the range of 6 to 10.

6. The process for preparing phosphine oxides according to claim 1, wherein said aprotic organic solvent does not dissolve aminophosphonium chlorides having the following formula (3):

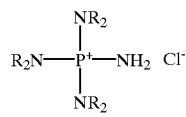

(3)

wherein R is the same as that of the formulae (1) and (2).

7. The process for preparing phosphine oxides according to claim 1, wherein said aprotic organic solvent does not dissolve aminophosphonium chlorides having the formula (3) and is substantially immiscible with water wherein formula (3) is as follows:

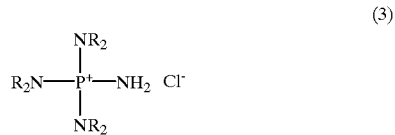

(3)

wherein R is the same as that of the formulae (1) and (2).

8. The process for preparing phosphine oxides according claim 7, wherein the number of moles of said iminophosphoranes having the formula (1) used per 1 mole of phosphorus oxytrichloride is in the range of 6 to 10.

9. The process for preparing phosphine oxides according claim 6, wherein the number of moles of said iminophosphoranes having the formula (1) used per 1 mole of phosphorus oxytrichloride is in the range of 6 to 10.

10. The process for preparing phosphine oxides according claim 3, wherein the number of moles of said iminophosphoranes having the formula (1) used per 1 mole of phosphorus oxytrichloride is in the range of 6 to 10.

11. The process for preparing phosphine oxides according claim 2, wherein the number of moles of said iminophosphoranes having the formula (1) used per 1 mole of phosphorus oxytrichloride is in the range of 6 to 10.

12. The process for preparing phosphine oxides according claim 1, wherein the number of moles of said iminophosphoranes having the formula (1) used per 1 mole of phosphorus oxytrichloride is in the range of 6 to 10.

* * * * *